(12) United States Patent
Bergeron

(10) Patent No.: US 12,376,870 B2
(45) Date of Patent: Aug. 5, 2025

(54) CHOKING INTERVENTION DEVICE

(71) Applicant: John Daniel Bergeron, Nelson, GA (US)

(72) Inventor: John Daniel Bergeron, Nelson, GA (US)

( * ) Notice: Subject to any disclaimer, the term of this patent is extended or adjusted under 35 U.S.C. 154(b) by 442 days.

(21) Appl. No.: 18/069,482

(22) Filed: Dec. 21, 2022

(65) Prior Publication Data

US 2024/0206898 A1    Jun. 27, 2024

(51) Int. Cl.
*A61B 17/24*  (2006.01)
*A61B 17/50*  (2006.01)
*A61M 16/00*  (2006.01)
*A61M 16/06*  (2006.01)

(52) U.S. Cl.
CPC ........... *A61B 17/24* (2013.01); *A61B 17/50* (2013.01); *A61M 16/0009* (2014.02); *A61M 16/0075* (2013.01); *A61M 16/0616* (2014.02); *A61M 16/0683* (2013.01)

(58) Field of Classification Search
CPC .... A61B 17/24; A61B 17/50; A61M 16/0009; A61M 16/0075; A61M 16/0616; A61M 16/0683
See application file for complete search history.

(56) References Cited

U.S. PATENT DOCUMENTS

| | | | | |
|---|---|---|---|---|
| 4,971,053 A | * | 11/1990 | Tarrats | A61B 17/50 128/206.28 |
| 2015/0190158 A1 | * | 7/2015 | Lih | A61M 16/0075 606/106 |
| 2020/0306420 A1 | * | 10/2020 | Carver | A61M 1/815 |

* cited by examiner

*Primary Examiner* — Mohamed G Gabr

(57) ABSTRACT

A choking intervention device for clearing a foreign object obstructing a breathing passage of a choking victim includes an assembly of one or more hollow vessels and a facemask configured to enclose a person's mouth and nose. The assembly includes a plurality of vessels configured to create a low-pressure environment within the assembly. The assembly contains a bottom opening which provides access to the low-pressure interior. The facemask is coupled to the bottom of the assembly and is configured to enclose the choking victim's mouth and nose. The body of the assembly is further of proper size and shape to allow an ordinary individual the ability to hold and use the assembly with one hand. Operation of this device has the unique advantage of pressing toward the victim which facilitates the creation of an airtight seal between the facemask and the victim's face.

24 Claims, 16 Drawing Sheets

CHOKING INTERVENTION DEVICE

BACKGROUND-PRIOR ART

The following is a tabulation of some prior art that presently appears relevant:

U.S. Patents

| U.S. Pat. No. | Kind Code | Issue Date | Patentee |
| --- | --- | --- | --- |
| 3,939,830 | A | 1976 Feb. 24 | Da Costa |
| 4,790,818 | A | 1988 Dec. 13 | Deluca, Fasano |
| 4,971,053 | A | 1990 Nov. 20 | Tarrats |
| 5,609,149 | A | 1997 Mar. 11 | Takach |
| 5,782,837 | A | 1998 Jul. 21 | York |
| 6,749,599 | B2 | 2004 Jun. 15 | Litkouhi, Deluca, Abplanalp |
| 6,986,773 | B1 | 2006 Jan. 17 | Manougian |
| 7,351,245 | B2 | 2008 Apr. 1 | Rozinsky |
| 8,876,838 | B2 | 2014 Nov. 4 | Winiarski |
| 9,820,773 | B2 | 2017 Nov. 21 | Lieser |
| 10,052,115 | B2 | 2018 Aug. 21 | Lih |
| 11,324,877 | B2 | 2022 May 10 | Carver |

U.S. patent application Publications

| Publication Nr. | Kind Code | Publ. Date | Applicant |
| --- | --- | --- | --- |
| — | | | |

Foreign Patent Documents

| Foreign Doc. Nr. | Country Code | Kind Code | Publ. Date | |
| --- | --- | --- | --- | --- |
| WO2012091949 | | A1 | 2012 Jul. 5 | Hooper |
| 102017115283 | DE | A1 | 2019 Jan. 10 | Brinkmann, Engelhardt |

FIELD OF THE INVENTION

The present disclosure generally relates to first aid devices, and more specifically to a device for removal of an object obstructing an airway.

BACKGROUND OF THE INVENTION

Choking due to airway obstruction is a leading cause of death. Thousands of people die in the United States every year due to choking, making it one of the top causes of death. In a choking situation the victim has very little time to receive treatment as a lack of oxygen can quickly lead to brain damage or death. Given this lack of time it is imperative that the victim be given first aid as soon as possible.

In many choking cases the first reaction of bystanders is to slap the victim on the back or attempt to perform the Heimlich maneuver. However, these efforts do not always work, may result in injury to the victim, or may not be an option at all. For various reasons the Heimlich maneuver may be impossible to perform. For instance, the victim may be pregnant or obese or there may be a lack of space or ability to position yourself in order to administer such maneuvers. In other cases, a bystander may not know how to properly perform the Heimlich maneuver successfully.

In those situations, a device capable of producing a suction effect can help dislodge the obstruction blocking the victim's airway. Given the importance of quickly clearing a choking victim's airway, having a simple device such as this on hand can mean the difference between life and death.

Many different such devices which use a vacuum or suction effect to clear a choking victim's airway are known in the prior art, but most are overly complicated, difficult to operate, or designed in a sub-optimal way. Most require two-handed operation to perform, with one hand holding the mask firmly over the victim's mouth and nose necessary to form an airtight seal with the other used to operate the mechanics of the device. This makes the goal of relieving a choking victims airway more difficult as it would be preferred to be able to operate the device with one hand while steadying the victims head with the other.

U.S. Pat. No. 10,052,115B2 to Lih describes a choking intervention device, marketed as the "LifeVac", that has several operational disadvantages. First, use of the device requires two hands to operate, one hand to hold the facemask in place and maintain the necessary airtight seal and the second hand to operate the device itself. Second, the device has the disadvantage of requiring two motions, one toward the victim's mouth to expel internal air from the device and then another away from the victim's mouth to develop the low pressure necessary for dislodging an obstruction. The second motion in which low pressure is developed, is directed away from the victim's face and not towards it, thus the pressure between the facemask and the victims face is negatively affected by the device's operation during this critical phase. As the device is retracted low internal pressure is developed which could help maintain the necessary airtight seal, however, at the beginning of this backward motion the pressure inside the device and throat of the victim are largely the same as the surrounding atmosphere and as such will not develop a sufficient internal low pressure to maintain an airtight seal until the device is significantly extended. It is therefore necessary to use two hands in order to effectively operate the device and maintain the required airtight seal around the victim's mouth and nose. As mentioned, the device has the disadvantage of requiring two motions, one downward and toward the victim to expel air from within the device and another away from the victim to create the low pressure necessary to dislodge the obstruction. The downward motion carries with it substantial risk. Since the downward motion to expel air from within the device must be done over the victim's mouth, there is a substantial risk that through ordinary use of the device, positive pressure be introduced into the victim's airways should the relief valve(s) fail. This would be unknown to the operator who may be causing more harm than good if such a failure were to occur.

U.S. Pat. No. 11,324,877B2 to Carver describes an "Airway Assist Device" that has similar disadvantages as the LifeVac discussed above as its operation is very similar. It requires two hands to operate in order to maintain a sufficient seal around the victim's mouth and nose and operation of the device involves pulling away from the victim like the LifeVac. Also, the device has to be depressed in order to displace air from inside the device in order to be able to then retract the handle and create the low pressure required, relying on relief valves to prevent positive pressure from being introduced to the victim's airways.

Other devices have the disadvantage of requiring a separate source of low pressure, such as an empty vessel, or a high-pressure vessel that can be used to create low pressure. U.S. Pat. No. 6,749,599B2 to Litkouhi, Deluca and Abplanalp teaches a device in which an evacuated canister is coupled to a facemask. The device is configured to puncture the canister at the appropriate time in order to supply the low pressure required for the device to operate. U.S. Pat. No. 8,876,838B2 to Winiarski teaches another device that employs a Venturi Vacuum pump, which uses a high-pressure canister to produce low pressure. The devices are coupled to a facemask for applying low air pressure to a victim's airways. These devices are useless in the event that their vessels have not maintained their desired pressure differentials at the time of a choking event or if their pressure vessels are released before the facemask is applied to the victim's face. Further, once their sources of pressure differential are exhausted, they are no longer useful.

Therefore, a simple device which can be operated with one hand, that requires just one motion and which is designed so that the operation of the device itself increases the pressure required to maintain an airtight seal around the victim's mouth and nose would be beneficial. It would also be beneficial to have a device that can be manually operated to develop the necessary low air pressure continuously without having to rely on an overly complicated pressure generating mechanism or storage container that is subject to fail or quickly be exhausted. In addition, a device in which a failure of relief valves poses very little increased risk to the victim would be beneficial.

SUMMARY

The present invention comprises a rescue device capable of assisting a choking victim by creating a suction effect that can be applied to a choking victim's airways to clear an obstruction. The device comprises an assembly of one or more hollow vessels which when properly configured can be used to manually produce a region of low air pressure within the device that can be applied to the breathing passages of a choking victim through a facemask. The near end of the device extends toward the victim where a facemask is connected in airtight fashion. Low pressure is generated within the device. The motion of the devices manual operation is towards the victim's face. The facemask and region of low-pressure within the device are in fluid communication with one another so that the low-pressure will extend through the device to the facemask and the victim's airways.

A principal object of the invention is to provide a choking intervention device in which the operation of the device mechanics is towards the victim and can be used with just one hand, unlike other choking intervention devices. This unique aspect of the invention gives the user much more control and chance of success by freeing their other hand to help steady the victims head as well as providing a better seal between the attached facemask and the victims face during the operational phase of the device, making it easier to achieve the goal of applying low air pressure to the victim's airways to remove an object obstructing their breathing passages.

A critical component in achieving the objective of generating the required negative pressure on a downward thrust or towards the victim's face in order to create the necessary seal between the attached facemask and the victim's face is that the portion of the device which extends towards the victims face through which the negative pressure is transmitted to the attached facemask and the victim's airways is attached on its far end to the far end of the expandable component of the device. When the operable portion of the device, connected to this expandable section, is thrust downward or towards the victims face, the portion of the device attached to the facemask acts as a support structure holding the far end of the expandable section or vessel stationary and opposing the forces generated by operating the device, so that the thrusting motion will extend the expandable section, creating the internal region of low air pressure while generating forces towards the victim's face creating and enhancing the required airtight seal between the facemask and the victim's face naturally.

In one exemplary embodiment an outer vessel has the ability to be manually extended thereby expanding its internal volume and creating a region of low pressure. A second inner vessel, which extends through the bottom of the outer vessel, has attached at its near end a facemask used to enclose the victim's mouth and nose. The internal volume of the inner vessel is connected in fluid communication with the internal volume of the outer vessel allowing the region of low air pressure to be transmitted through it and the facemask to the airways of a choking victim. The internal volume of the outer vessel can be made to expand through a variety of means as will be shown by the following descriptions and drawings.

The present invention differs from other devices found in the prior art in that operation of the device pushes towards the victim's face during the critical phase of low-pressure generation. This beneficial motion towards the victim naturally increases the pressure between the attached facemask and the victims face improving the airtight seal required for the device to operate effectively and allowing for one-handed operation unlike other such devices found in the prior art. In addition, the retraction phase in which any positive pressure may be generated within the device occurs while the operator is pulling away from the victim's face. As such, normal operation of the device poses very little risk of introducing positive pressure to the victim's breathing passages. In addition to employing one way relief valves to minimize the risk of any positive pressure reaching the victim's breathing passages, the action of retracting the device itself reduces the pressure between the facemask and the victim's face substantially reducing the airtight seal and naturally avoiding any positive pressure from being directed into the victim's breathing passages.

Accordingly, the present invention has the following advantages: the device can be operated with one hand leaving the other free to help steady the victims head, manual operation of the device is beneficial to accomplishing the goal of clearing a victim's airways by increasing the pressure required to maintain an airtight seal between the facemask and the victim's face during the critical phase of low pressure generation, operation of the device poses very little risk of introducing positive air pressure to the victims airways regardless of any potential failure of any part or component, the device is relatively simple to construct and manufacture making it cost effective, the device can be used manually to produce low pressure repeatedly and does not rely on any pressurized or empty container which may lose their required pressure differentials prior to being used, the device can be used by the victim themselves, and the device parts can be made of low-cost, durable and commonly available materials which do not degrade over time.

The foregoing and other objects are intended to be illustrative of the invention and are not meant in a limiting sense. Many possible embodiments of the invention may be made and will be readily evident upon a study of the full specification and accompanying drawings comprising a part thereof. Various features and sub-combinations of invention may be employed without reference to other features and sub-combinations. Other objects and advantages of this invention will become apparent and are disclosed throughout other areas of the specification, drawings and claims.

BRIEF DESCRIPTION OF THE DRAWINGS

These and other features, aspects, and advantages of the present invention will become better understood with regard to the following description, appended claims, and accompanying drawings, wherein:

DETAILED DESCRIPTION OF THE INVENTION

Figure 1:
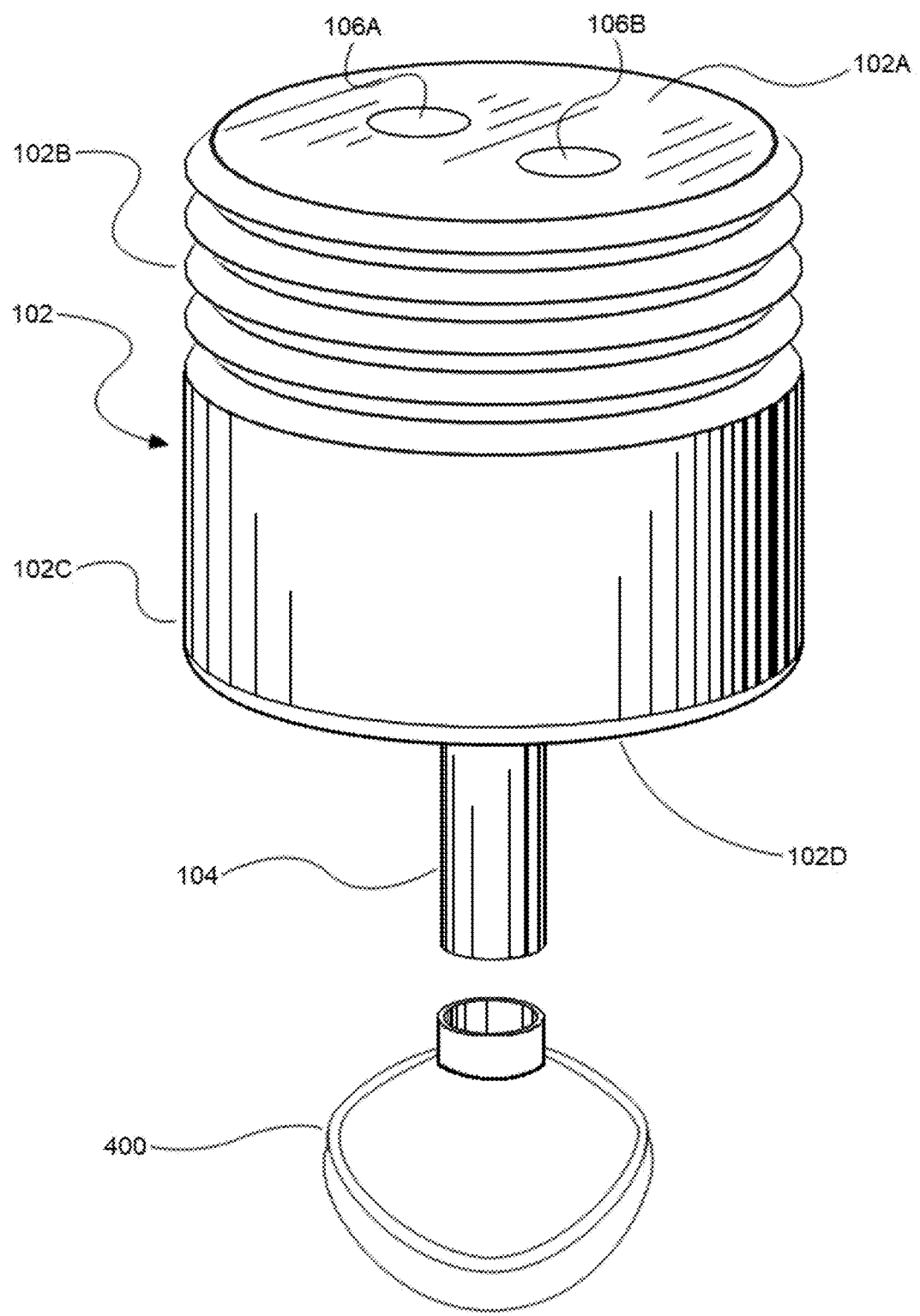
FIG. 1 illustrates an isometric view of an exemplary embodiment of a choking intervention device.
Figure 2:
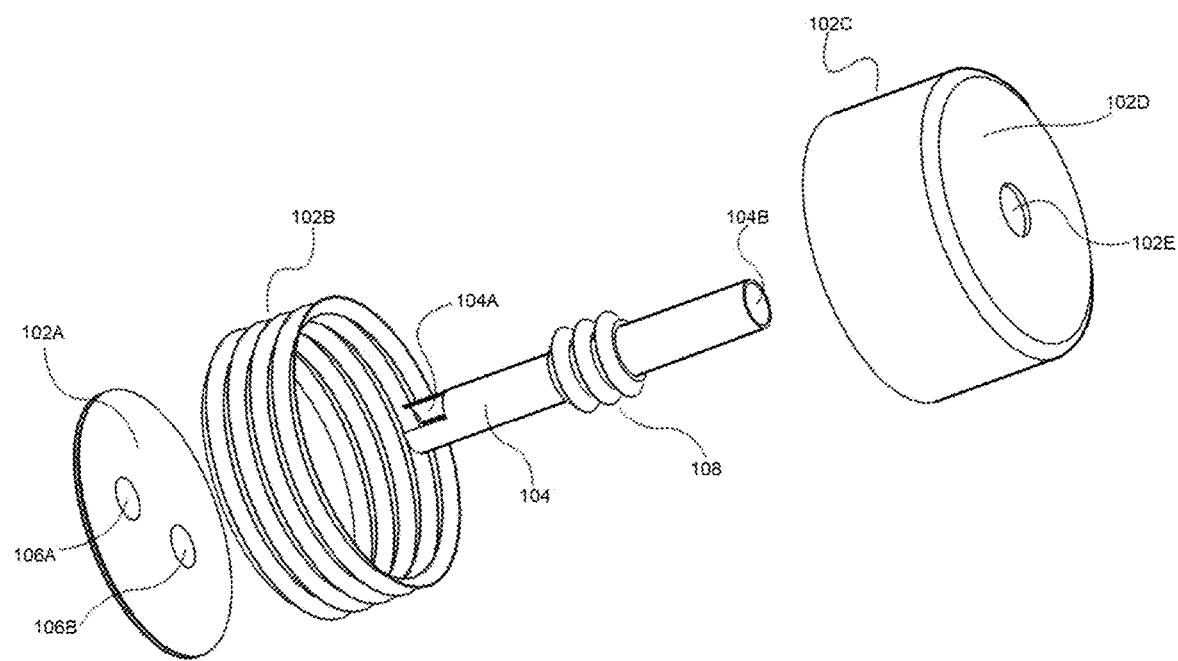
FIG. 2 illustrates an exploded view of exemplary embodiment of FIG. 1.
Figure 3:
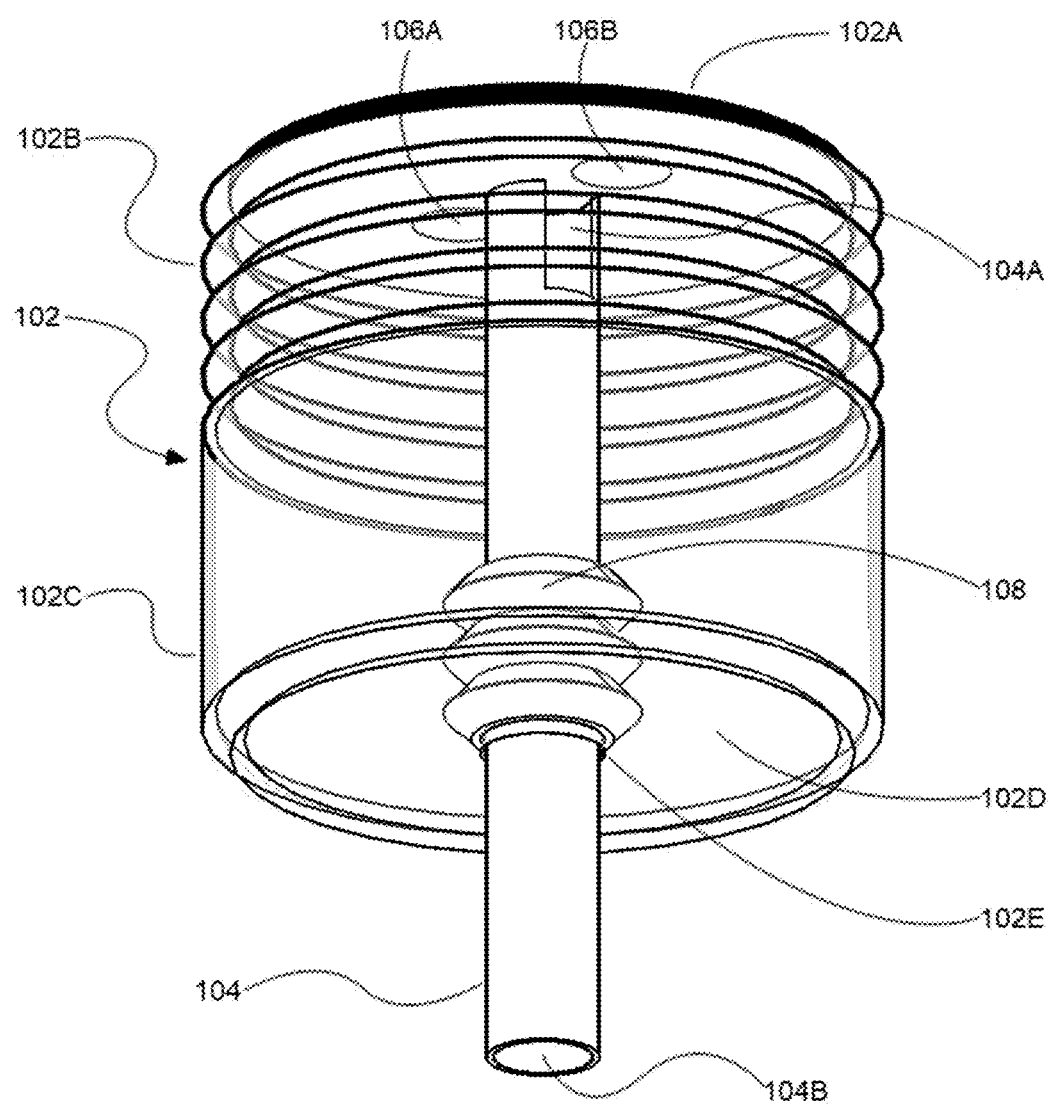
FIG. 3 illustrates an isometric view of exemplary embodiment of FIG. 1 with transparent outer vessel showing its interior.
Figure 4:
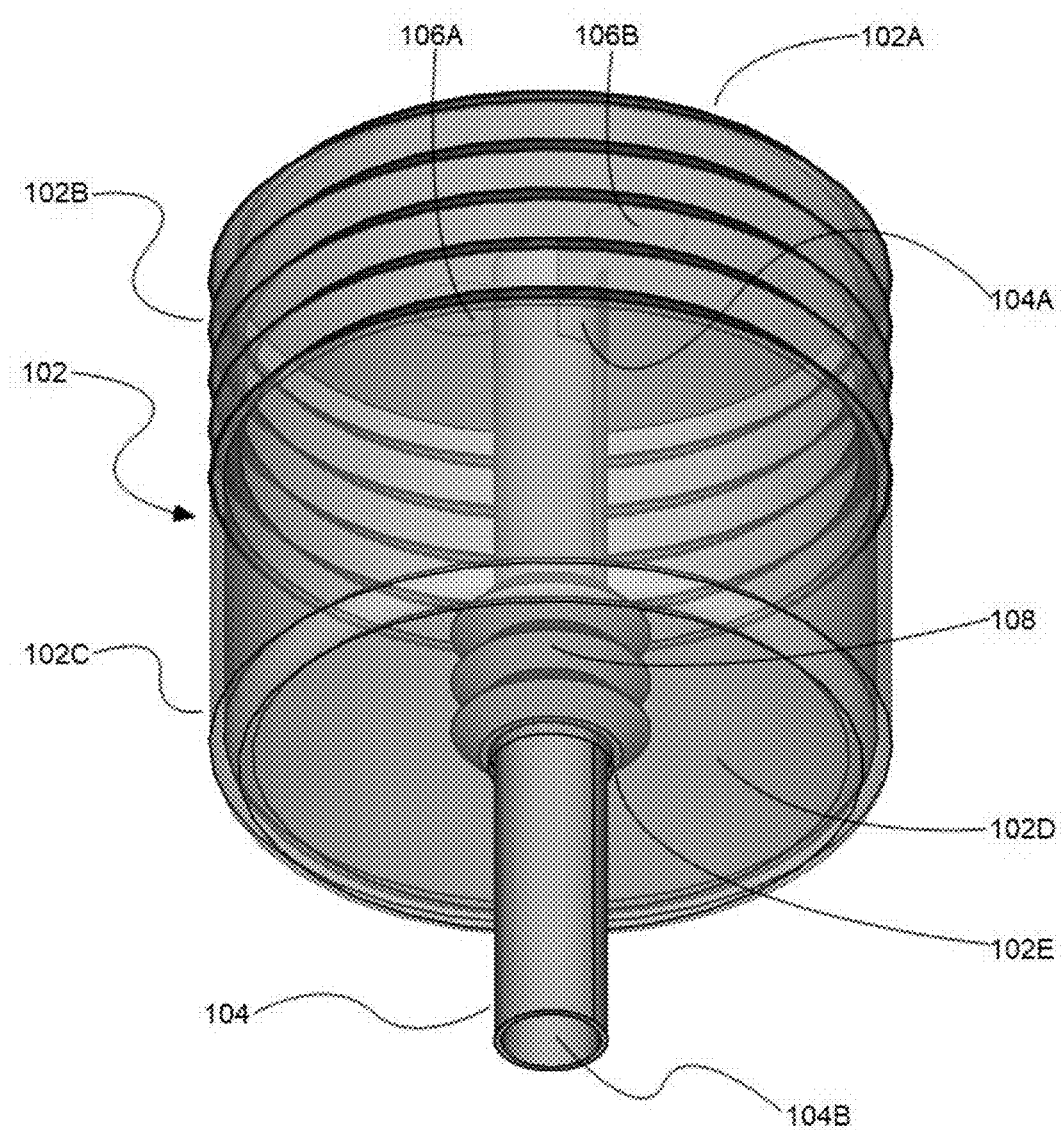
FIG. 4 illustrates a shaded isometric view of exemplary embodiment of FIG. 1 with transparent outer vessel showing its interior.
Figure 5:
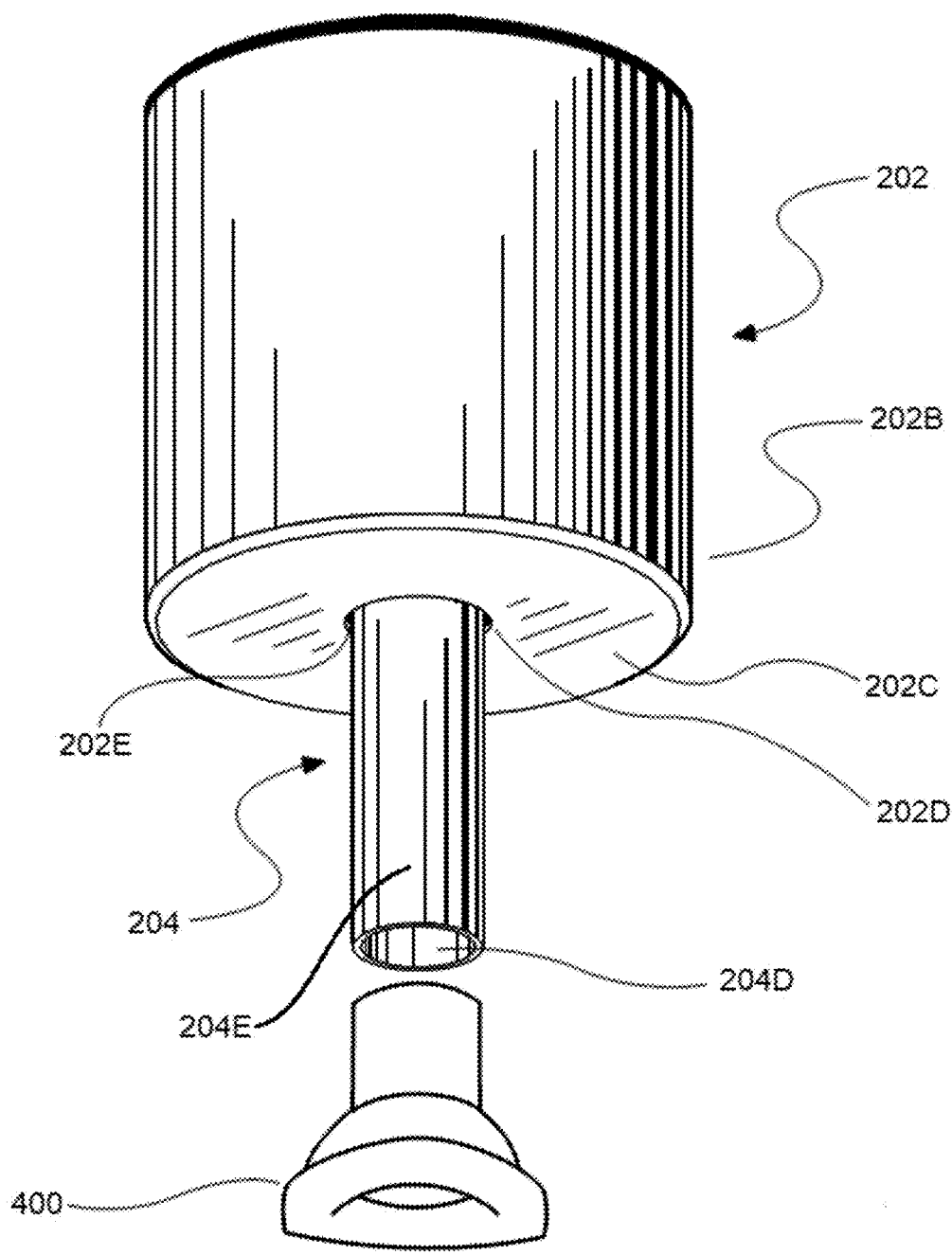
FIG. 5 illustrates an isometric view of an exemplary embodiment of a choking intervention device.

The various examples disclosed herein generally relate to first aid devices and more particularly to devices and methods for removal of an object obstructing an airway. The choking intervention devices described herein are used for clearing an object obstructing a breathing passage of a choking victim. The victim's mouth and nose are enclosed with the choking intervention device providing an airtight interface between the device and the victim. When the operable portion of the device is thrust towards the victim's face as designed the object is dislodged from the breathing passage of the victim.

While the disclosed embodiments may be considered preferred, it is to be understood that these embodiments are merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately configured structure. Notably, as will become apparent after thorough study of this specification and accompanying drawings, the position of vessels within the device need not be as depicted. Specifically, the device does not require an inner vessel be positioned in the center of an outer vessel, or even enclosed at all, to be able to function and produce the negative pressure in a way that is conducive to the goal of dislodging a foreign body from a choking victim's airways. In fact, a device constructed of only one properly shaped vessel can be envisioned with the same basic principles as what is described herein.

Referring generally to FIGS. 1-8, which depict exemplary embodiments of a choking intervention device, the particular embodiments comprise two hollow vessels, having one larger outer vessel and one smaller inner vessel. Each vessel is further designed to work with the other to produce a region of low pressure through the use of airtight connections between the two vessels forming a single dynamic device. When properly configured, these two vessels, together with their airtight connections, can be used to form an internal volume of low air pressure that can be applied to the breathing passage of a choking victim and dislodge the obstruction.

Now referring specifically to FIGS. 1-4, the exemplary embodiment depicted comprises an outer vessel 102 enclosing an inner vessel 104 which extends beyond and through outer vessel end opening 102E within outer vessel bottom face 102D. Inner vessel 104 further has an opening 104B on its near end to which facemask 400 can be connected in airtight fashion and used to place over a choking victim's mouth and nose. When outer vessel body bottom 102C of outer vessel 102 is thrust onto inner vessel 104 and towards the choking victims face, the internal volume of outer vessel 102 expands creating a region of low air pressure within the internal volume of outer vessel 102. This region of low pressure is in fluid communication with the interior of inner vessel 104 through inner vessel openings 104A or other suitable openings within the portion of the wall of inner vessel 104 that is enclosed by outer vessel 102. The low pressure then extends through inner vessel openings 104A and the interior of inner vessel 104 to attached face mask 400 thereby providing low pressure to the breathing passage of the choking victim and dislodging the obstruction.

Again, referring to FIGS. 1-4, in the particular embodiment depicted, outer vessel 102 further comprises an airtight assembly composed of parts outer vessel top cap 102A, expandable outer vessel body top accordion 102B, outer vessel body bottom 102C and outer vessel bottom face 102D. The depicted embodiments further include expandable inner accordion 108 coupled directly and in airtight fashion around the perimeter of its bottom end to outer vessel end opening 102E and directly and in airtight fashion around the perimeter of its top end to the outer wall of inner vessel 104. The depicted embodiments further include the direct attachment of inner vessel 104 at its top end to the bottom face of outer vessel top cap 102A. The depicted embodiments further show inner vessel openings 104A adjacent to the bottom face of outer vessel top cap 102A. Thus, the internal volume of outer vessel 102 is a sealed volume in which negative air pressure can only be transmitted through inner vessel openings 104A, providing the airtight properties required to allow the formation of sufficient internal negative pressure required by the device. It should be noted that all components of outer vessel 102 can be joined through various means including, but not limited to, gluing, welding, friction-fitting, snap-fitting, threaded mating, clasps or the like. These same means can be used to join all components of the device including attaching the bottom end of inner accordion 108 to outer vessel end opening 102E, attaching the top end of inner accordion 108 to the outer wall of inner vessel 104 and attaching the top end of inner vessel 104 to the bottom face of outer vessel top cap 102A. In addition, any combination of the components of the device could be constructed as a single piece instead of as individual pieces.

Again, referring to FIGS. 1-4, both outer vessel body top accordion 102B and inner accordion 108 can be made from any semi-rigid material suitable to allow them to extend or flex longitudinally along the axis of the device while largely retaining their shape and rigidity. This assembly of parts produces a dynamic device in which the outer vessel body bottom 102C of outer vessel 102 can extend to grow its internal volume and thereby produce an internal region of low air pressure. This region of low air pressure extends through inner vessel openings 104A to inner vessel 104 and through attached facemask 400 to the victim's airways.

In some embodiments the parts 102B and 108 depicted in FIGS. 1-4 could alternatively be made of a different extendable structure or material capable of longitudinal expansion along the axis of the device and allow outer vessel body bottom 102C to extend while still maintaining both an airtight internal volume and the necessary structural integrity required to develop the necessary internal region of low air pressure. Many different solutions for this extension can be envisioned and should be apparent to those skilled in the art. The embodiments depicted are merely for illustration purposes only and not intended in a limiting sense.

Now referring specifically to FIGS. 5-8, the exemplary embodiment depicted comprises outer vessel 202 enclosing inner vessel 204 whose body 204E extends beyond and through outer vessel end opening 202D within outer vessel bottom face 202C. Inner vessel 204 further has an opening 204D on its near end to which an airtight facemask can be connected in airtight fashion and used to place over a choking victim's mouth and nose. When outer vessel 202 is thrust onto inner vessel body 204E and towards the choking victims face, the internal volume of the lower portion of outer vessel 202 expands creating a region of low pressure. This region of low pressure is in fluid communication with the interior of inner vessel 204 through inner vessel openings 204C or other suitable openings within the portion of the wall of inner vessel body 204E that is enclosed by outer vessel 202. The low pressure then extends through the inner vessel openings 204C and the interior of inner vessel body 204E to the attached face mask thereby providing low pressure to the breathing passages of the choking victim and dislodging the obstruction.

Again, referring to FIGS. 5-8, in the particular embodiment depicted, outer vessel 202 further comprises an airtight assembly composed of parts outer vessel body 202B and outer vessel bottom face 202C enclosing the top portion of inner vessel 204. Enclosed inner vessel 204 has at its top end inner vessel piston head 204A that fits snugly inside the walls of outer vessel 202. The near end of outer vessel 202 has outer vessel end opening 202D through which inner vessel body 204E fits snugly in airtight fashion and extends beyond and through outer vessel end opening 202D within outer vessel bottom face 202C. The exemplary embodiment depicted shows two critical joints between outer vessel 202 and inner vessel 204. On its top end, between inner vessel piston head 204A and the interior wall of outer vessel body 202B, we see depicted inner vessel piston head interface 204B. On its near end between outer vessel end opening 202D and the outer walls of inner vessel body 204E is depicted outer vessel end opening interface 202E. Each interface where the two vessels meet utilizes a material that allows each vessel to slide relative to the other while maintaining an airtight seal. Also, on the top portion of inner vessel 204 enclosed within the walls of outer vessel 202 we see inner vessel opening 204C adjacent to inner vessel piston head 204A which allows fluid communication between the internal volume of the lower portion of outer vessel 202 and the interior of inner vessel 204. Each vessel is uniform along its operable length which allows the vessels to slide smoothly together and onto one another while maintaining their airtight interfaces thus forming an airtight internal volume in the lower portion of outer vessel 202 between the outside wall of inner vessel body 204E, the inside bottom wall of inner vessel piston head 204A, the inside wall of the lower portion of outer vessel body 202B, the inside top wall of outer vessel bottom face 202C and terminating at outer vessel end opening 202D. This internal volume is a sealed volume in which negative air pressure is generated and can only be transmitted through inner vessel opening 204C, providing the airtight properties required to allow the formation of sufficient internal negative pressure required by the device. This produces a dynamic assembly in which outer vessel 202 can be thrust onto inner vessel 204 to grow the internal volume of the lower portion of outer vessel 202 and produce a region of low air pressure. It should be noted that all components of outer vessel 202 can be joined through various means including, but not limited to, gluing, welding, friction-fitting, snap-fitting, threaded mating, clasps or the like. These same means can be used to join components of inner vessel 204 together. In addition, any combination of the components of either outer vessel 204 or inner vessel 202 could be constructed as a single piece instead of as individual pieces.

Also depicted is outer vessel top cap 202A with outer vessel top cap opening 202F. It should be noted that this part is there only for structural support or illustration but is not required for the exemplary embodiment depicted to function properly. Outer vessel top cap opening 202F allows for the free motion of outer vessel 202 relative to inner vessel 204 and prevents any pressure differential from accumulating in the top portion of outer vessel 202 above inner vessel piston head 204A.

Figure 9:
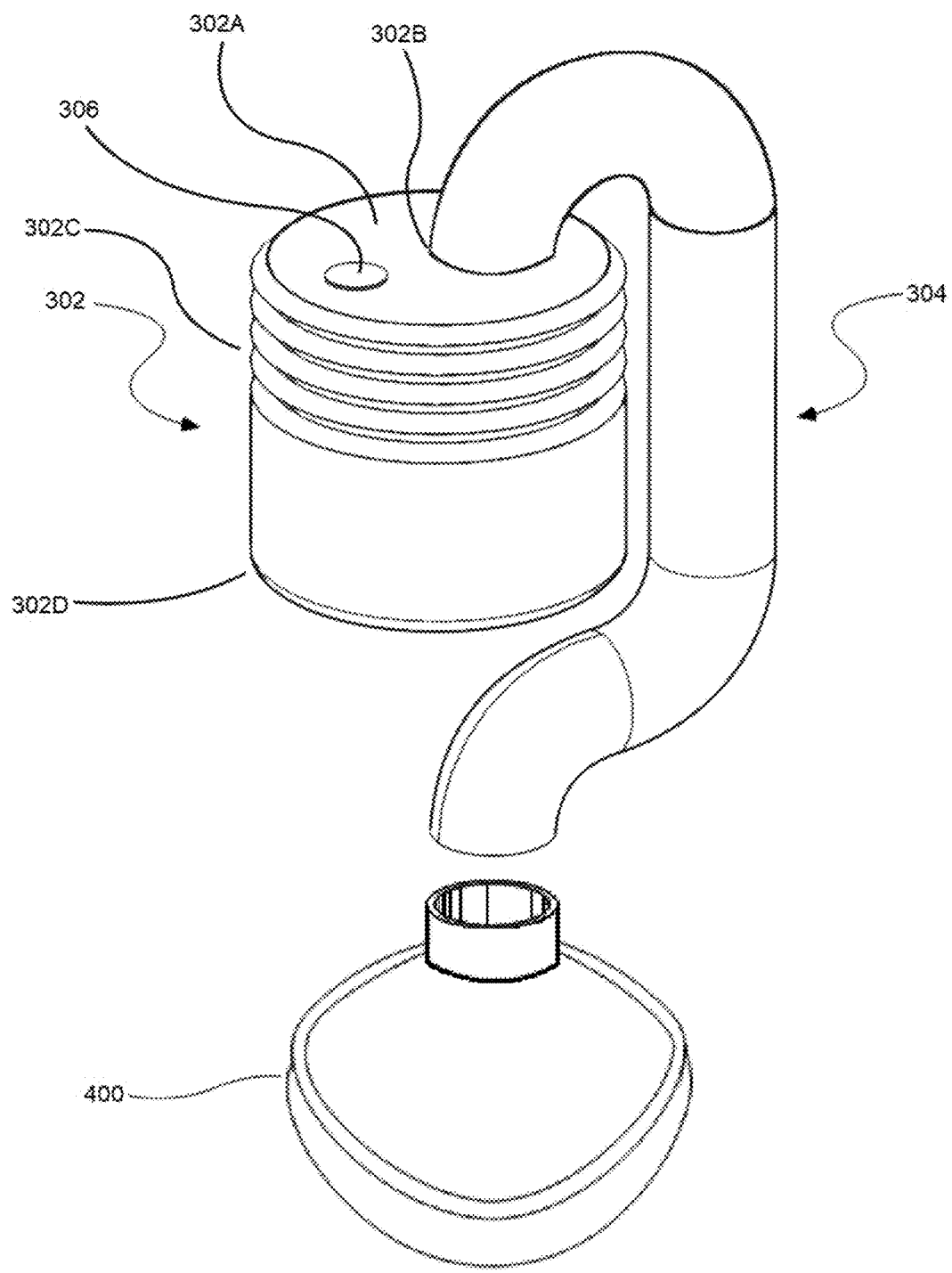
FIG. 9 illustrates an isometric view of an exemplary embodiment of a choking intervention device.
Figure 10:
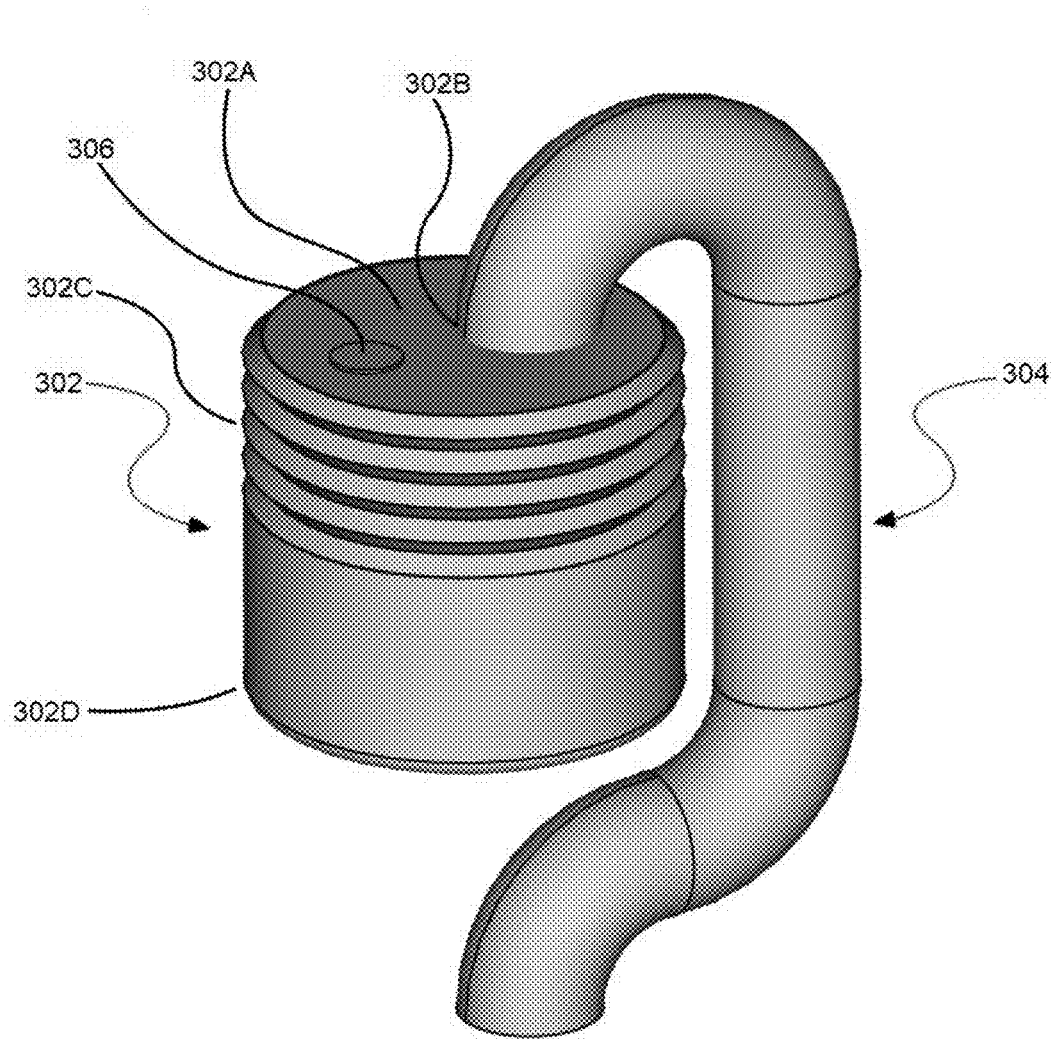
FIG. 10 illustrates a shaded isometric view of exemplary embodiment of FIG. 9.
Figure 11:
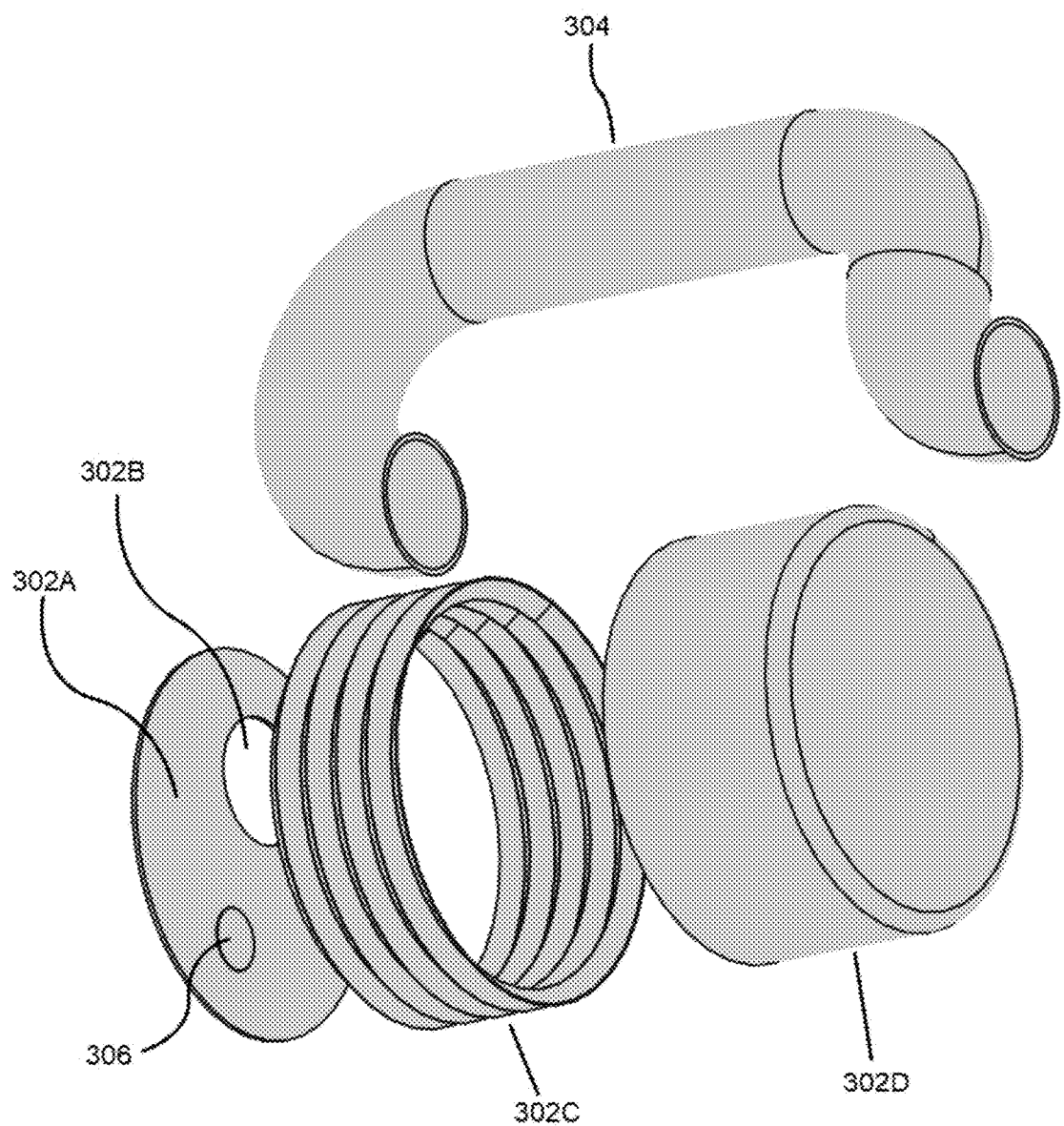
FIG. 11 illustrates an exploded view of exemplary embodiment of FIG. 9.

Now referring specifically to FIGS. 9-11, the exemplary embodiment depicted comprises expandable vessel 302 connected on its top end to hollow tube 304 which follows a path that redirects underneath and terminates below said expandable vessel 302 where facemask 400 can be attached. This shape and configuration, like the other embodiments allows operation of the device to be directed towards the victim's face. Unlike the previously described exemplary embodiments, FIGS. 9-11 show how an area of low air pressure can be directed to the victim's airways without an inner vessel being enclosed within an outer vessel. However, the principal of operation is the same, one portion of the device is designed to expand creating a region of low air pressure and the operation of this mechanism is directed towards the victim's face. The region of low air pressure follows an airtight pathway from the internal volume of expandable vessel 302 through hollow tube 304 and to facemask 400 where it can be used to introduce low air pressure to the breathing passages of a choking victim.

Again, referring to FIGS. 9-11, in the particular embodiments depicted, expandable vessel 302 further comprises an airtight assembly composed of parts expandable vessel top cap 302A, expandable vessel body top accordion 302C and expandable vessel body bottom 302D. Within expandable vessel top cap 302A we also see expandable vessel top cap opening 302B, where hollow tube 304 is attached in airtight fashion. Thus, the internal volume of expandable vessel 302 is a sealed volume in which negative air pressure can only be transmitted through expandable vessel top cap opening 302B, providing the airtight properties required to allow the formation of sufficient internal negative pressure required by the device. It should be noted that all components of expandable vessel 302 can be joined through various means including, but not limited to, gluing, welding, friction-fitting, snap-fitting, threaded mating, clasps or the like. These same means can be used to join all components of the device including attaching hollow tube 304 to expandable vessel top cap opening 302B. In addition, any combination of the components of the device could be constructed as a single piece instead of as individual pieces.

As previously mentioned, numerous solutions can be envisioned to facilitate the expansion mechanism required by this device. Referring to FIGS. 12-16, we see illustrated two other possible configurations that allow the expansion function. The first utilizes a flexible material at the top end of the expandable section capable of longitudinal expansion or elastic extension along the axis of the device while maintaining the structural integrity necessary to allow the development of an Internal region of low pressure. The second utilizes a configuration in which the expandable section is composed of two parts, an upper and lower part which overlap one another in airtight fashion allowing the lower part to be extended and develop the necessary region of low air pressure within the device.

Figure 12:
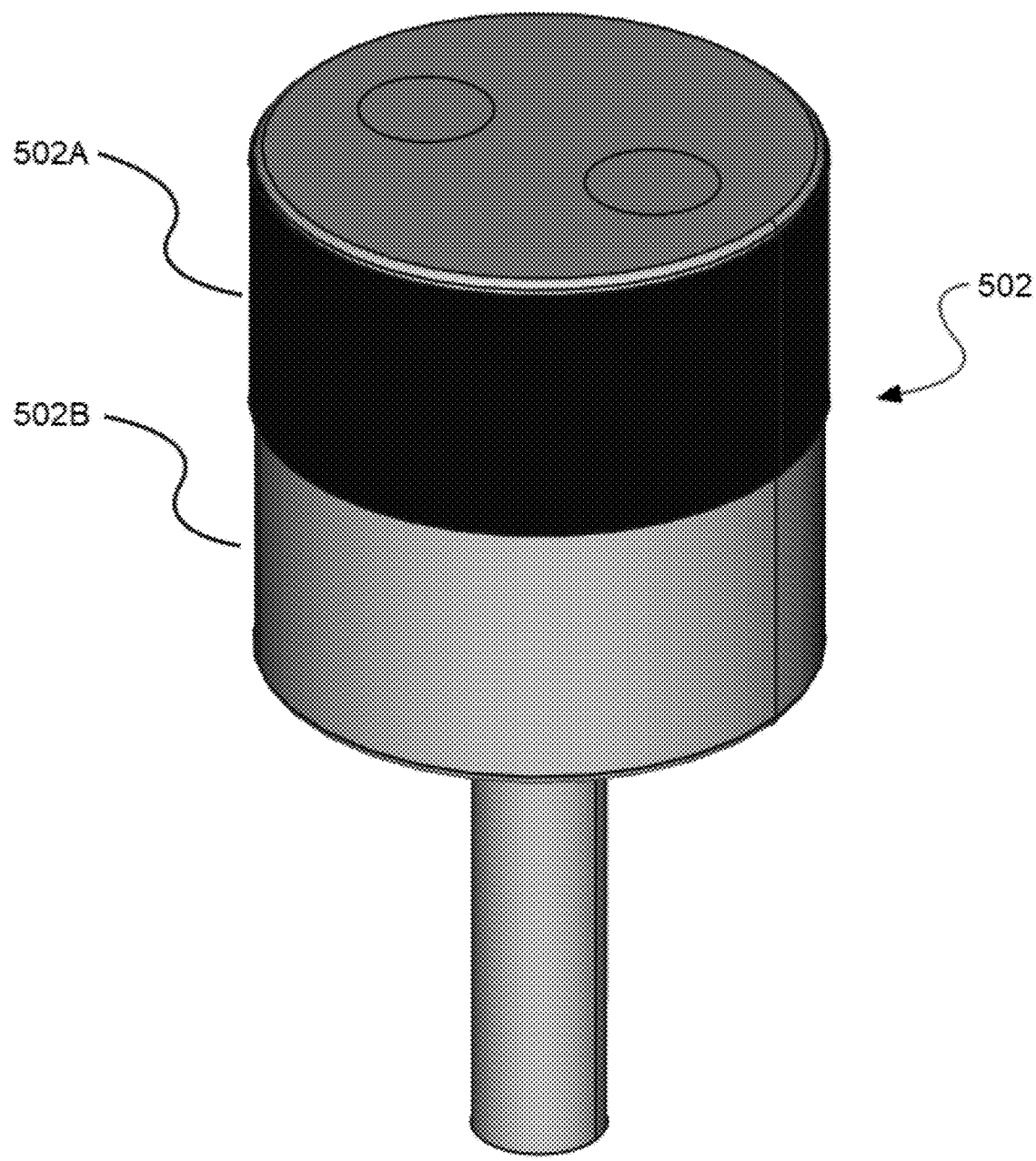
FIG. 12 illustrates and isometric view of an exemplary embodiment of a choking intervention device.
Figure 13:
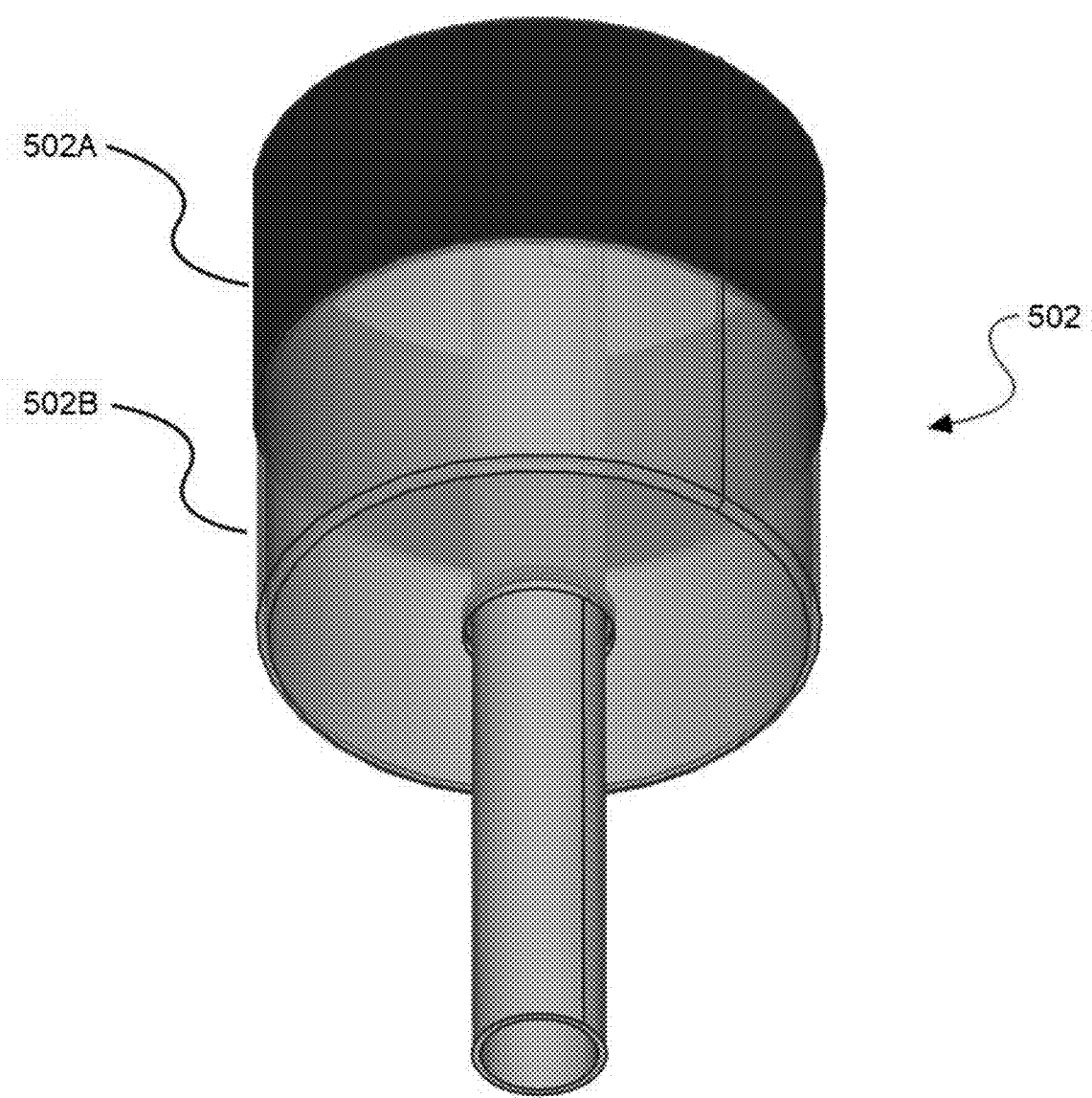
FIG. 13 illustrates an isometric view of exemplary embodiment of FIG. 12 with transparent outer vessel showing its interior.

Now referring specifically to FIGS. 12 and 13, the exemplary embodiment depicted illustrates expandable vessel body 502 composed of parts expandable vessel body top 502A and expandable vessel body bottom 502B. This discussion is limited to only the function of these two parts to facilitate the necessary expansion function. Other parts illustrated are to be understood to function as described previously in this specification. In this configuration, expandable vessel body top 502A and expandable vessel body bottom 502B are joined together at their ends in airtight fashion creating a single piece to compose expandable vessel body 502. In the depicted embodiment, expandable vessel body top 502A is made of an elastic material capable of longitudinal expansion or extension along the axis of the device allowing the operation of the device by grasping expandable vessel body bottom 502B and thrusting towards the victim as described previously. It should be noted this same configuration can be used in previously described embodiments including the embodiment depicted in FIGS. 1-4 and 9-11.

Figure 14:
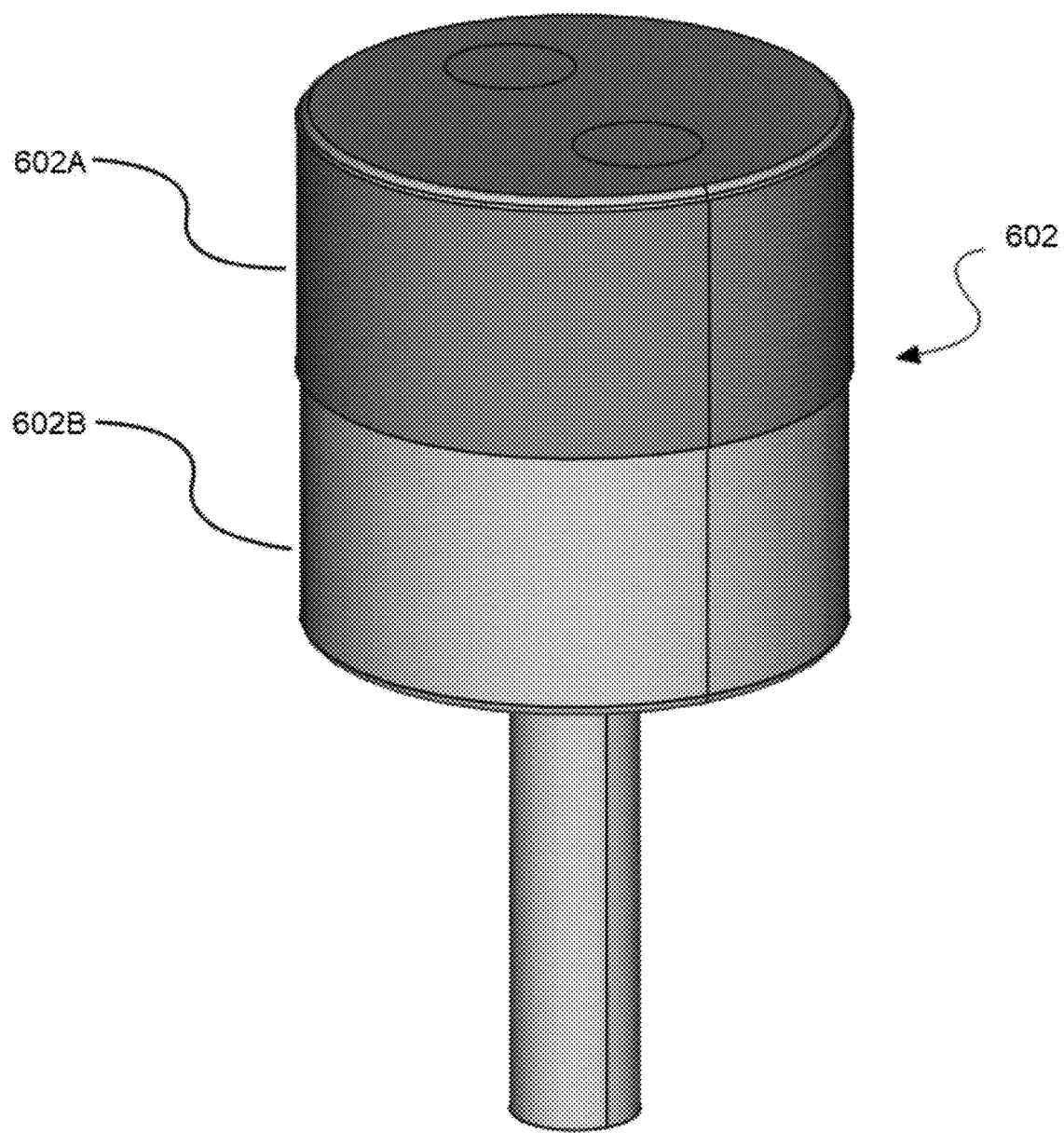
FIG. 14 illustrates an isometric view of an exemplary embodiment of a choking intervention device.
Figure 15:
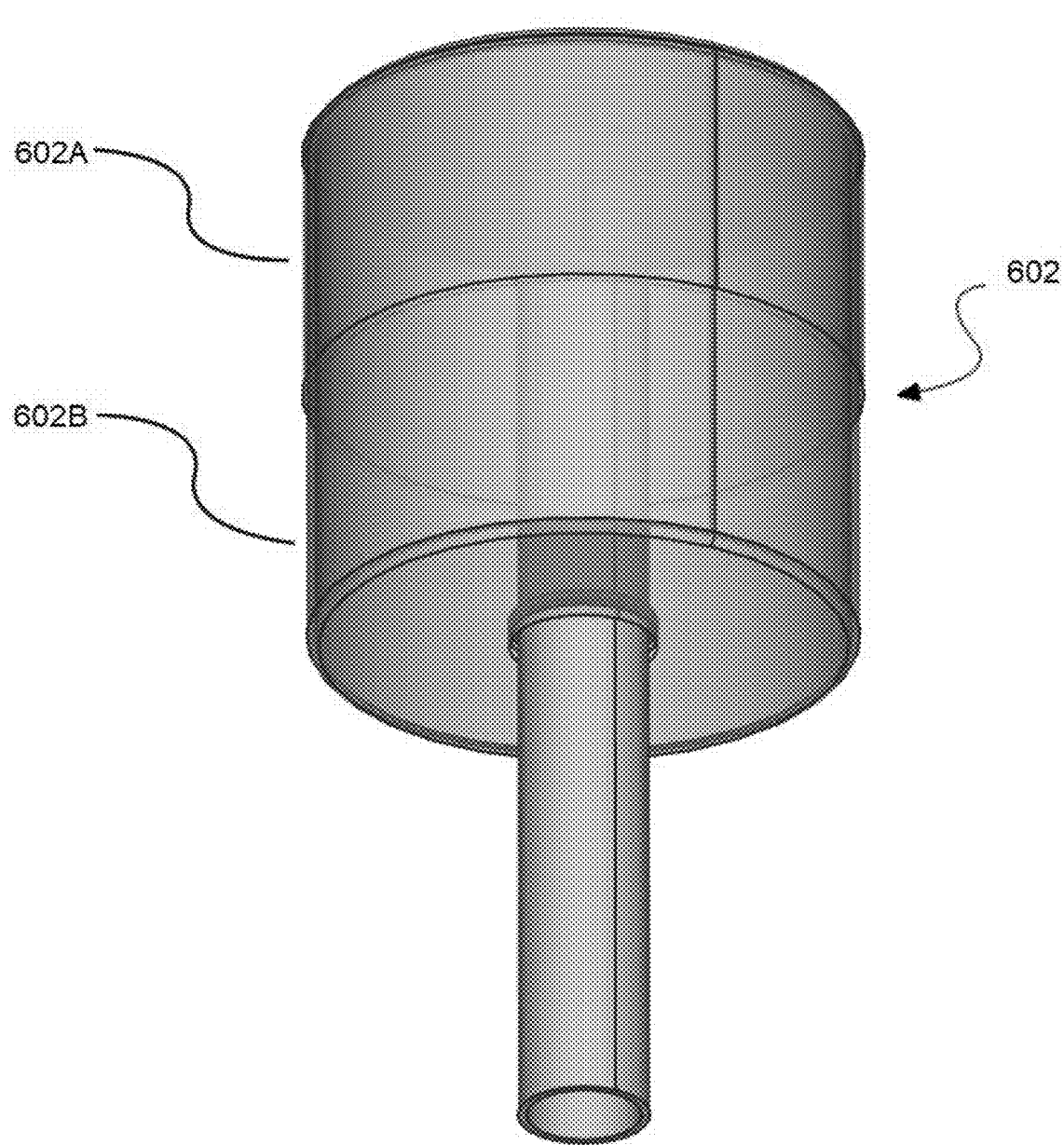
FIG. 15 illustrates an isometric view of exemplary embodiment of FIG. 14 with transparent outer vessel showing its interior.
Figure 16:
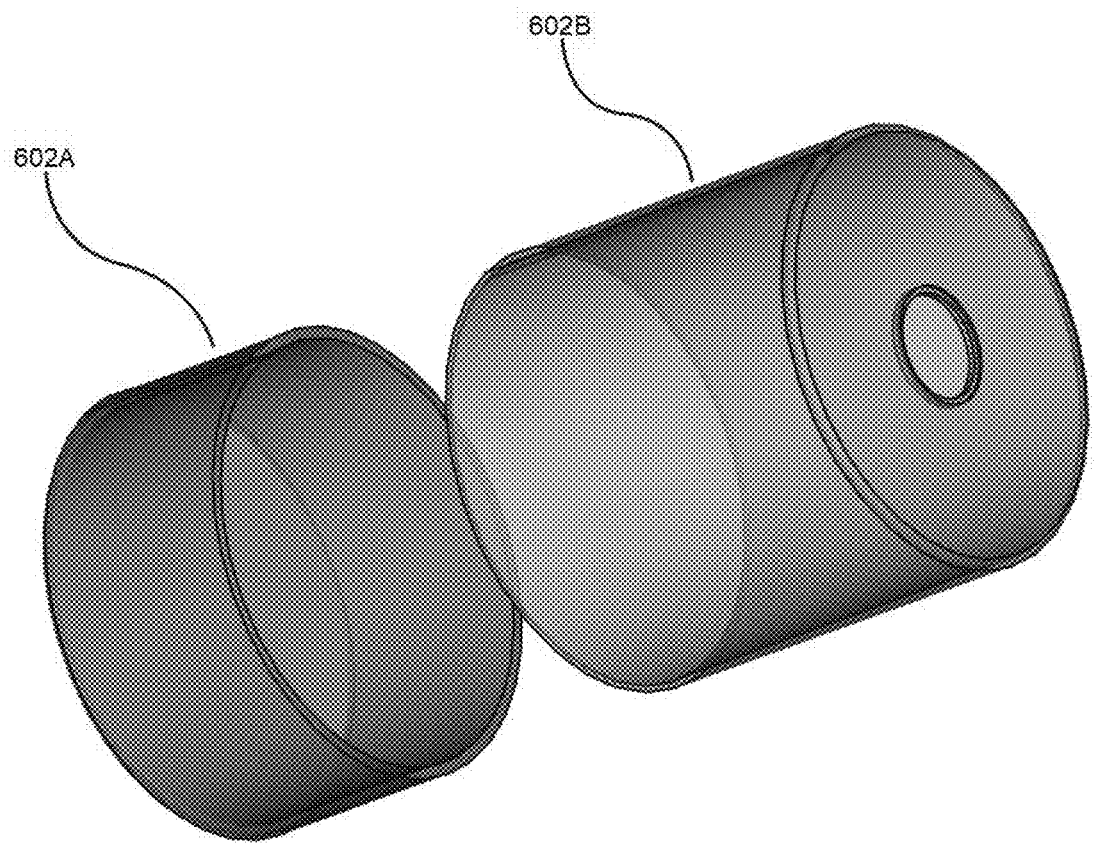
FIG. 16 illustrates an exploded view of exemplary embodiment of FIG. 14.

Now referring specifically to FIGS. 14-16, the exemplary embodiment depicted illustrates expandable vessel body 602 composed of parts expandable vessel body top 602A and expandable vessel body bottom 602B. This discussion is limited to only the function of these two parts to facilitate the necessary expansion function. Other parts illustrated are to be understood to function as described previously in this specification. In this configuration, expandable vessel body top 602A and expandable vessel body bottom 602B are configured to overlap one another in airtight fashion to compose expandable vessel body 602. In the depicted embodiment, expandable vessel body top 602A overlaps expandable vessel body bottom 602B. This configuration allows operation of the device by grasping expandable vessel body bottom 602B and thrusting towards the victim as described previously. It is not important whether expandable vessel body top 602A overlaps expandable vessel body bottom 602B or vice versa. All that is required is an airtight Interface between the two that is maintained as the device is operated. It should be noted this same configuration can be used in previously described embodiments including the embodiment depicted in FIGS. 1-4 and 9-11.

Figure 6:
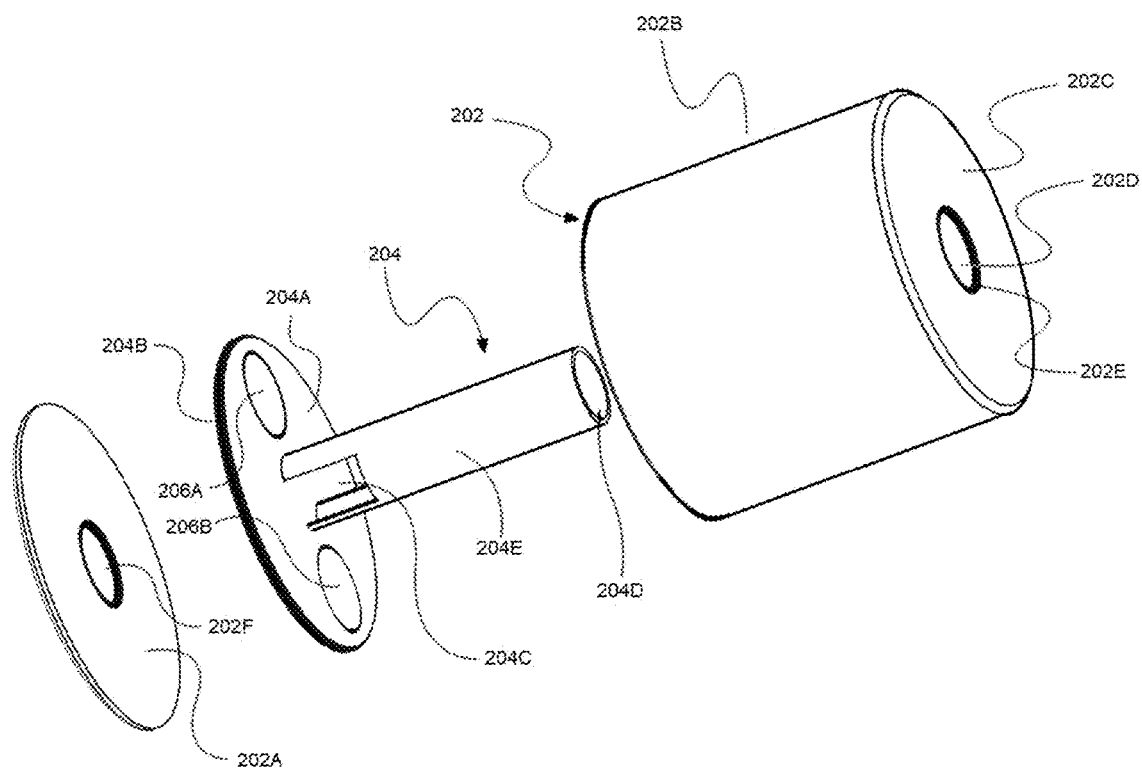
FIG. 6 illustrates an exploded view of exemplary embodiment of FIG. 5.
Figure 7:
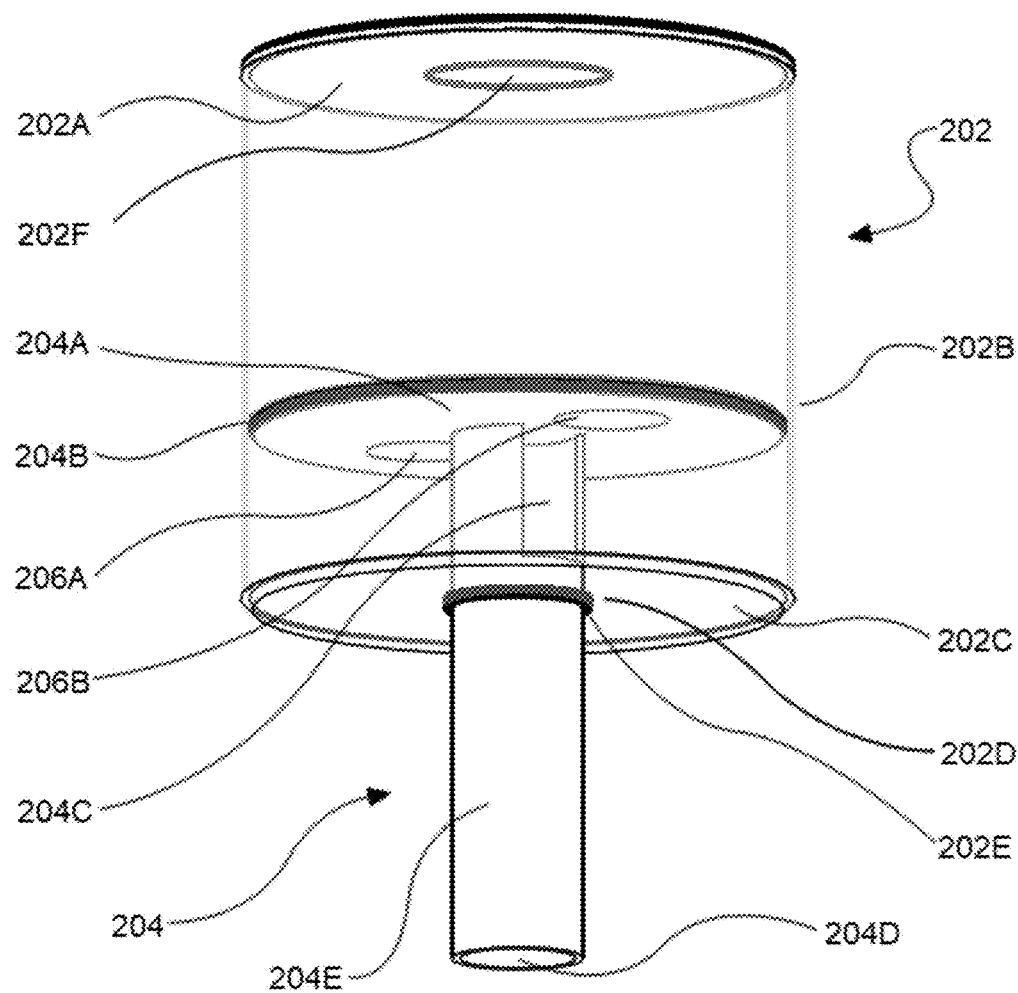
FIG. 7 illustrates an isometric view of exemplary embodiment of FIG. 5 having transparent views of its interior.
Figure 8:
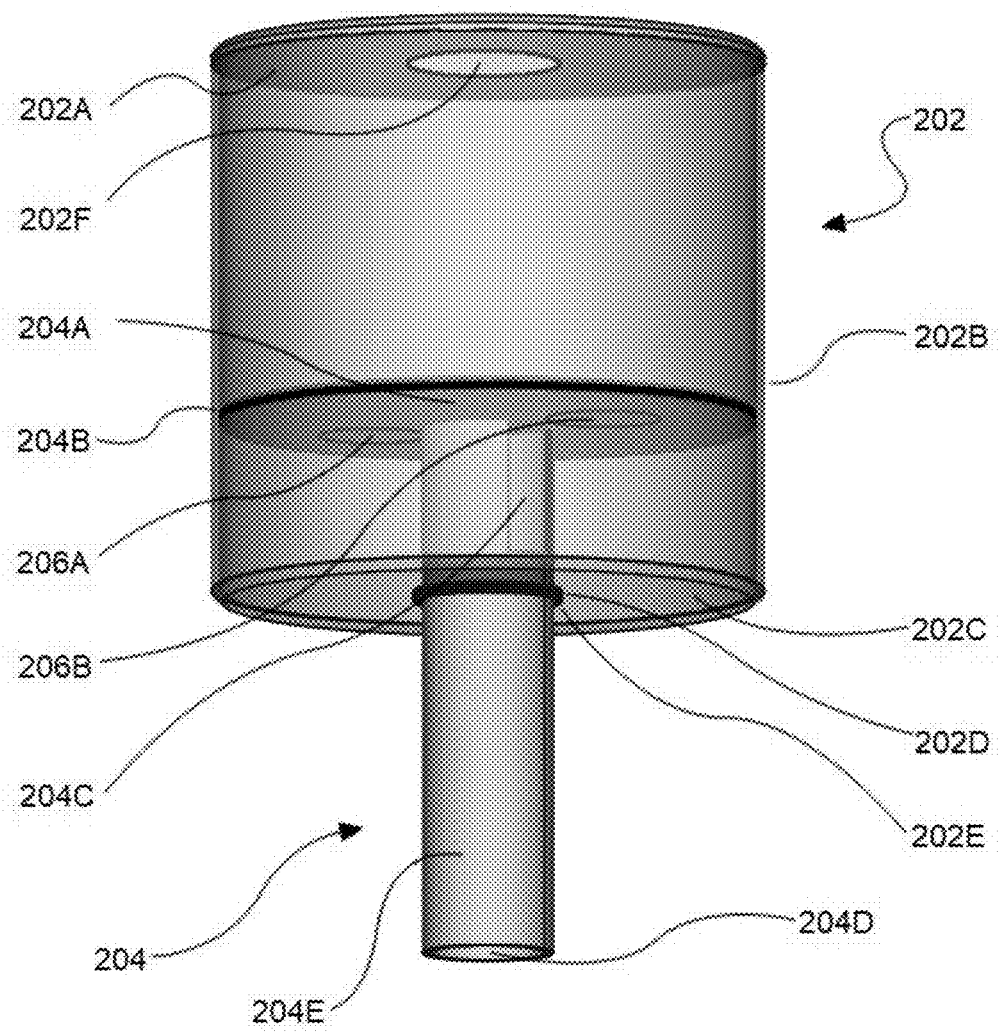
FIG. 8 illustrates a shaded isometric view of exemplary embodiment of FIG. 5 having transparent views of its interior.

In some embodiments, the choking intervention device may further include one or more relief valves. In FIGS. 1-4 the depicted embodiment shows relief valves 106A and 106B positioned on outer vessel top cap 102A. The valves limit fluid communication of the low air pressure region as required. During normal operation in which outer vessel body bottom 102C is thrust onto inner vessel 104 and towards the victim's face and low pressure is generated in the interior of outer vessel 102, the relief valves will close and low air pressure will be directed to facemask 400. During the subsequent release phase as the device is released and the internal volume of outer vessel 102 is reduced, the relief valves will open releasing any positive pressure thus preventing positive pressure from entering the victim's airways. In FIGS. 6-8 relief valves are similarly illustrated within inner vessel piston head 204A. The valves limit fluid communication of the low air pressure region as required. During normal operation in which outer vessel body 202B is thrust onto inner vessel body 204E and towards the victim's face and low pressure is generated in the internal volume of the lower portion of outer vessel 202, the relief valves will close and low air pressure will be directed to facemask 400. During the subsequent release phase as the device is released and the internal volume of the lower portion of outer vessel 202 is reduced, the relief valves will open releasing any positive pressure thus preventing positive pressure from entering the victim's airways. In FIGS. 9-11 relief valve 306 is similarly illustrated within expandable vessel top cap 302A. The valve limits fluid communication of the low air pressure region as required. During normal operation in which expandable vessel body bottom 302D is thrust towards the victim's face and low pressure is generated in its interior the relief valve will close and low air pressure will be directed to facemask 400. During the subsequent release phase as the device is released and the internal volume of outer vessel 302 is reduced, the relief valves will open releasing any positive pressure thus preventing positive pressure from entering the victim's airways.

In other embodiments, the choking intervention device further includes a one-way valve within the interior of inner vessels 104 and 204 and within hollow tube 304 which further prevent positive pressure from entering the airways of the choking victim. Any suitable type of relief valve can be used for any of these in any suitable position on or within the device.

It should be noted that while the components of the embodiments depicted are cylindrical in shape, in practice these components could be virtually any shape sufficient to allow one or more properly shaped and configured vessels to create the necessary region of low air pressure useful for dislodging an obstruction from a choking victim's airways.

Also discussed is a method of clearing an object obstructing a breathing passage of a choking victim using a device comprising one or more vessels configured to create a region of low air pressure coupled to a facemask.

With appropriate facemask attached, the device is positioned over the victim's face where a seal is provided between the facemask and the victims face, enclosing the mouth and nose in airtight fashion. The operable portion of the device is thrust towards the choking victims face, expanding the internal volume within the device creating a region of low internal pressure. The victim's airways being directly connected to this region of low pressure are then cleared of the obstruction. The steps can be repeated until the obstruction is dislodged.

What is claimed is:

1. A choking intervention device, comprising:
    an assembly of hollow vessels configured to produce low air pressure that can be used to clear an object obstructing a breathing passage of a choking victim comprising:
    an inner and outer vessel joined together to create a single dynamic device for producing low air pressure having one vessel longer than the other and extending towards the victim through which said low air pressure is transmitted;
    a means by which the internal volume of the device can be made to expand creating a region of low air pressure, wherein operation of said means is configured to be thrust towards the victim with one hand;
    a graspable section connected to or forming a part of said expansion means used to operate the device;
    a set of one or more openings within the walls of the portion of said inner vessel fully enclosed by said outer vessel allowing fluid communication between inside of said outer vessel and the inside of said inner vessel;
    an opening on the near end of said longer vessel, on the near end of the device, configured to provide fluid access to the internal volume of the assembly and dimensioned to be attached to a facemask via a facemask connector where a facemask can be attached in airtight fashion;
    an airtight pathway from said region of low air pressure within the device to said near end opening and attached facemask;
    a seal between attached facemask and the victims face resulting from the forces generated during said thrusting motion of the device;
    wherein an airtight internal volume is formed within the device where low air pressure is generated and transmitted to the opening on the near end of the device where an attached facemask can be used to transmit low air pressure to the breathing passages of a choking victim configured in such a way that operation of the device is toward the victim's face forming an airtight seal between attached face mask and victim's face due to the resulting pressure thus requiring only one hand to operate.

2. The choking intervention device of claim 1 further comprising an expandable component which facilitates said expansion means.

3. The choking intervention device of claim 2 wherein said expandable component further comprises a semi-rigid accordion capable of extension allowing for said expansion of said internal volume.

4. The choking intervention device of claim 2 wherein said expandable component further comprises an elastic material capable of extension allowing for said expansion of said internal volume.

5. The choking intervention device of claim 2 wherein said expandable component further comprises two overlapping and corresponding parts upper and lower in which one part overlaps the other in airtight fashion with sufficient overlap to allow lower portion to extend thereby allowing for said expansion of said internal volume.

6. The choking intervention device of claim 1 further comprising a piston disposed within said vessel having said expandable volume capable of expanding said internal volume.

7. The choking intervention device of claim 1 wherein there exists an opening at the bottom end of said outer vessel which fits snugly and in airtight fashion over the exterior wall of said inner vessel where said inner vessel extends through and past near end opening of said outer vessel having an airtight interface between said inner vessel outer wall and said outer vessel near end opening which allows outer vessel to slide relative to inner vessel while maintaining said airtight interface.

8. The choking intervention device of claim 1 wherein there exists an opening at the bottom end of said outer vessel which is connected to a medial position on the outer wall of said inner vessel by a flexible and airtight material where said inner vessel extends through and past the near end of said outer vessel toward the victim which allows outer vessel to extend relative to inner vessel while maintaining an airtight seal between said outer vessel end opening and said medial position on the outer wall of said inner vessel.

9. The choking intervention device of claim 1 wherein one or more relief valves are configured to allow air to escape from inside the device when in retraction phase and prevent air from entering the device when in operation phase thus preventing positive pressure from being introduced to the choking victim's airways and only allowing negative pressure to be introduced to the choking victim's airways.

10. The choking intervention device of claim 1 further comprising an interchangeable facemask coupled in airtight fashion to said bottom end opening and configured to enclose the choking victim's mouth and nose wherein facemask further comprises a seal adapted to provide an airtight interface between the facemask and a face of the victim when the facemask is placed over the choking victim's mouth and nose.

11. A choking intervention device, comprising:
    a single properly shaped vessel configured to produce low air pressure that can be used to clear an object obstructing a breathing passage of a choking victim comprising:
    a means by which the internal volume of said vessel can expand creating a region of low air pressure within the device, wherein operation of said means is configured to be thrust towards the victim and can be operated with one hand;
    a graspable section connected to or forming a part of said expansion means used to operate the device;
    a portion of said vessel that extends from top of said expandable section, shaped so that said vessel along with its internal volume turns back and is redirected beneath said graspable section and extends toward the choking victim's face;
    an opening on the near end of the device configured to provide fluid access to said internal volume of the device and dimensioned to be attached to a facemask via a facemask connector where a facemask can be attached in airtight fashion;
    an airtight pathway from said region of low air pressure within the device through said top vessel extension to said near end opening and attached facemask;
    wherein an airtight internal volume is formed within the device where low air pressure is generated and transmitted to the opening on the near end of the device where an attached facemask can be used to transmit low air pressure to the breathing passages of a choking victim configured in such a way that its operation is toward the victim's face forming an airtight seal between attached face mask and victim's face due to the resulting pressure thus requiring only one hand to operate.

12. The choking intervention device of claim 11 further comprising an expandable component of said vessel which facilitates said expansion means.

13. The choking intervention device of claim 12 wherein said expandable component further comprises a semi-rigid accordion capable of extension allowing for said expansion of said internal volume.

14. The choking intervention device of claim 12 wherein said expandable component further comprises an elastic material capable of extension allowing for said expansion of said internal volume.

15. The choking intervention device of claim 12 wherein said expandable component further comprises two overlapping and corresponding parts upper and lower in which one part overlaps the other in airtight fashion with sufficient overlap to allow lower portion to extend allowing for said expansion of said internal volume.

16. The choking intervention device of claim 11 further comprising a piston disposed within said vessel connected to said graspable section which can be used to withdraw said piston within vessel thereby allowing for said expansion of said internal volume.

17. The choking intervention device of claim 11 wherein one or more relief valves are configured to allow air to escape from inside the device when in retraction phase and prevent air from entering the device when in operation phase thus preventing positive pressure from being introduced to the choking victim's airways and only allowing negative pressure to be introduced to the choking victim's airways.

18. The choking intervention device of claim 11 further comprising an interchangeable facemask coupled in airtight fashion to said bottom end opening and configured to enclose the choking victim's mouth and nose wherein facemask further comprises a seal adapted to provide an airtight interface between the facemask and a face of the victim when the facemask is placed over the choking victim's mouth and nose.

19. A choking intervention device, comprising:
an assembly of hollow vessels configured to produce low air pressure that can be used to clear an object obstructing a breathing passage of a choking victim comprising:
an inner and outer vessel configured to work together to create a single dynamic device for producing low air pressure wherein said inner vessel extends below and past the bottom of said outer vessel and towards the victim through which low air pressure is transmitted;
a property wherein said outer vessel can slide over said inner vessel and towards the victim providing a means to expand the internal volume of said outer vessel creating a region of low air pressure within the device, wherein operation of said means is configured to be thrust towards the victim and can be operated with one hand;
a graspable section connected to or forming a part of said outer vessel used to operate the device;
a set of one or more openings within the walls of the portion of said inner vessel fully enclosed by said outer vessel allowing fluid communication between said internal volume of said outer vessel and the inside of said inner vessel;
an opening on the near end of the device configured to provide fluid access to the internal volume of the assembly and dimensioned to be attached to a facemask via a facemask connector where a facemask can be attached in airtight fashion;
an airtight pathway from said region of low air pressure within the device to said near end opening and attached facemask;
a seal between attached facemask and the victims face resulting from the forces generated by operating the device;
wherein an airtight internal volume is formed within the device where low air pressure is generated and transmitted to the opening on the near end of the device where an attached facemask can be used to transmit low air pressure to the breathing passages of a choking victim configured in such a way that operation of the device is toward the victim's face forming an airtight seal between attached face mask and victim's face due to the resulting pressure thus requiring only one hand to operate.

20. The choking intervention device of claim 19 wherein there is a head or shape on the top end of said inner vessel which fits snugly and in airtight fashion within interior wall of said outer vessel and composing the top of said outer vessel internal volume having an airtight interface between said head or shape on the top end of said inner vessel and interior wall of said outer vessel which allows outer vessel to slide relative to inner vessel while maintaining said airtight interface.

21. The choking intervention device of claim 19 wherein there exists an opening at the bottom end of said outer vessel which fits snugly and in airtight fashion over the exterior wall of said inner vessel where said inner vessel extends through and past near end opening of said outer vessel having an airtight interface between said inner vessel outer wall and said outer vessel near end opening which allows outer vessel to slide relative to inner vessel while maintaining said airtight interface.

22. The choking intervention device of claim 19 wherein there exists an opening at the bottom end of said outer vessel which is connected to a medial position on the outer wall of said inner vessel by a flexible and airtight material where said inner vessel extends through and past the near end of said outer vessel toward the victim which allows outer vessel to extend relative to inner vessel while maintaining an airtight seal between said outer vessel end opening and said medial position on the outer wall of said inner vessel.

23. The choking intervention device of claim 19 wherein one or more relief valves are configured to allow air to escape from inside the device when in retraction phase and prevent air from entering the device when in operation phase thus preventing positive pressure from being introduced to the choking victim's airways and only allowing negative pressure to be introduced to the choking victim's airways.

24. The choking intervention device of claim 19 further comprising an interchangeable facemask coupled in airtight fashion to said bottom end opening and configured to enclose the choking victim's mouth and nose wherein facemask further comprises a seal adapted to provide an airtight interface between the facemask and a face of the victim when the facemask is placed over the choking victim's mouth and nose.

\* \* \* \* \*